United States Patent
Kerr et al.

(10) Patent No.: US 7,111,517 B2
(45) Date of Patent: Sep. 26, 2006

(54) APPARATUS AND METHOD FOR IN-SITU MEASURING OF VIBRATIONAL ENERGY IN A PROCESS BATH OF A VIBRATIONAL CLEANING SYSTEM

(75) Inventors: Daniel Charles Kerr, Orlando, FL (US); Alan R. Olds, Clermont, FL (US); Bradley Curtis Deselms, Longwood, FL (US); Dennis P. Biondi, Cocoa, FL (US); William A. Russell, Orlando, FL (US)

(73) Assignee: Agere Systems, Inc., Allentown, PA (US)

( * ) Notice: Subject to any disclaimer, the term of this patent is extended or adjusted under 35 U.S.C. 154(b) by 32 days.

(21) Appl. No.: 10/902,332

(22) Filed: Jul. 29, 2004

(65) Prior Publication Data
US 2006/0021439 A1    Feb. 2, 2006

(51) Int. Cl.
*B08B 3/12* (2006.01)
(52) U.S. Cl. ............ 73/648; 134/57 R; 134/113; 134/184; 134/902
(58) Field of Classification Search .......... 73/645, 73/646, 647, 648
See application file for complete search history.

(56) References Cited

U.S. PATENT DOCUMENTS

| | | | | |
|---|---|---|---|---|
| 4,962,776 A | * | 10/1990 | Liu et al. ............. | 134/11 |
| 5,931,173 A | * | 8/1999 | Schiele ................ | 134/57 R |
| 6,109,113 A | * | 8/2000 | Chavan et al. ........ | 73/718 |
| 6,420,201 B1 | | 7/2002 | Webster | |
| 6,445,053 B1 | | 9/2002 | Cho | |
| 6,450,184 B1 | | 9/2002 | Azar | |
| 6,557,654 B1 | * | 5/2003 | Murray ................ | 134/1.3 |
| 6,629,465 B1 | | 10/2003 | Maluf et al. | |
| 6,691,578 B1 | | 2/2004 | Puskas | |

FOREIGN PATENT DOCUMENTS

JP        55159121 A   * 12/1980

* cited by examiner

*Primary Examiner*—Hezron Williams
*Assistant Examiner*—Rose M. Miller
(74) *Attorney, Agent, or Firm*—Duane Morris LLP

(57) ABSTRACT

Apparatus and method are provided for in-situ measurement of vibrational energy applied to a wafer in a process bath of a vibrational cleaning system. The apparatus may be made up of a test wafer comprising an array of pressure sensing elements disposed thereon for monitoring power level variation of a time-varying pressure wave. The time-varying pressure wave is indicative of vibrational energy that would be applied to a wafer in the process bath in the position of the test wafer.

20 Claims, 1 Drawing Sheet

APPARATUS AND METHOD FOR IN-SITU MEASURING OF VIBRATIONAL ENERGY IN A PROCESS BATH OF A VIBRATIONAL CLEANING SYSTEM

FIELD OF THE INVENTION

This invention relates generally to the field of semiconductor manufacturing, and, more particularly, to apparatus and method for in-situ measuring of vibrational energy in a process bath of a vibrational cleaning system for semiconductor wafers.

BACKGROUND OF THE INVENTION

Vibrational scrubbing of wafers, such as ultrasonic or megasonic scrubbing operations, is a well-known, non-contact and brushless technique for removing particles from a semiconductor wafer. During a typical vibrational scrubbing operation, a plurality of wafers is immersed in a process bath, such as comprising a suitable liquid medium, to which vibrational energy is applied. In an ultrasonic operation, the vibrational energy is typically applied at frequencies less than about 400 kHz, while in a megasonic operation the frequencies may range from 700 kHz to 1.2 MHz. High intensity sound waves generate pressure fluctuations that produce millions of microscopic bubbles in the liquid medium. These bubbles rapidly form and collapse (a mechanism called cavitation), producing shock waves that impinge on wafer surfaces. These shock waves displace or loosen particulates that may be present on such wafer surfaces.

A need that arises in these vibrational processes is being able to accurately and consistently maintain an appropriate level of vibrational energy. For example, damage to semiconductor features may occur if the level of vibrational power imparted during a cleaning cycle is excessive. Conversely, if the power setting is too low, then particle removal may be degraded.

It is further desirable to measure the vibrational energy for supporting basic tasks, such as process checks of a vibrational cleaning system that may be performed from time to time. Another desirable capability would be determining effects of different process tools in the process bath. These effects could be baselined and reduced if, for example, one had the ability of measuring and maintaining a desired level of vibrational energy notwithstanding the presence of any such different process tools in the process bath. More importantly, it is desirable to be able to determine the actual degree of sonic vibrational energy delivered to various locations on a surface of a wafer being cleaned in the sonic bath.

Known pressure-sensing devices, such as may comprise a pressure sensor positioned at a distal end of a wand, commonly suffer from inaccuracies due to variations in the vibrational energy pattern that is formed in the process bath. Attempts to overcome the inaccuracies of use of a test wand involve the measurement of vibrational energy at numerous locations in the sonic bath and plotting of the energy distribution on graphs. However, at megasonic frequencies, the wand can affect the energy levels at the measuring location. Further, unless there are products to be cleaned in the sonic bath at the time of measurement, the actual energy delivered will be different from the measured energy. For example, the vibrational energy pattern may be affected based on the physical structures that may be present in the process bath, such as the presence or absence of wafers, inter-wafer spacing, the physical characteristics of a mounting structure for the wafers, the configuration of the pressure-sensing device, the presence or absence of the pressure-sensing device, etc.

Another known technique for determining the level of vibrational energy in the process bath may require the use of a test wafer. That is, a wafer especially prepared with a predefined amount and type of particles. The test wafer is then subjected to various levels of vibrational energy and evaluated after each test to determine particle removal efficiency. This technique may suffer from various limitations such as the following: 1) in practical implementations only certain types of particles may be prepared on the wafer (e.g., nitride or carbide-based particles); 2) adhesion forces between the wafer surface and the particles may be highly variable depending on the shape of the particles, the specific mechanism used for adhering the particles, etc.; 3) the process tank will be contaminated with particles after each test; 4) application of the particles to the surfaces of the test wafer is typically performed manually and is highly variable depending on the specific operator performing the application, and the variation from operator to operator may exist even when using a standard set of instructions; 5) a common technique for applying the particles may require burdensome and careful handling (e.g., dropping nitride particles onto a wafer spinning at a relatively high speed); 6) manufacturing and handling of the test wafer may involve contamination of tools that will require burdensome cleansing before reuse; and 7) inability to identify situations in which the presence of excessive vibrational energy might damage a wafer.

BRIEF DESCRIPTION OF THE DRAWINGS

The features and advantages of the present invention will become apparent from the following detailed description of the invention when read with the accompanying drawings in which.

DETAILED DESCRIPTION OF THE INVENTION

Figure 1:
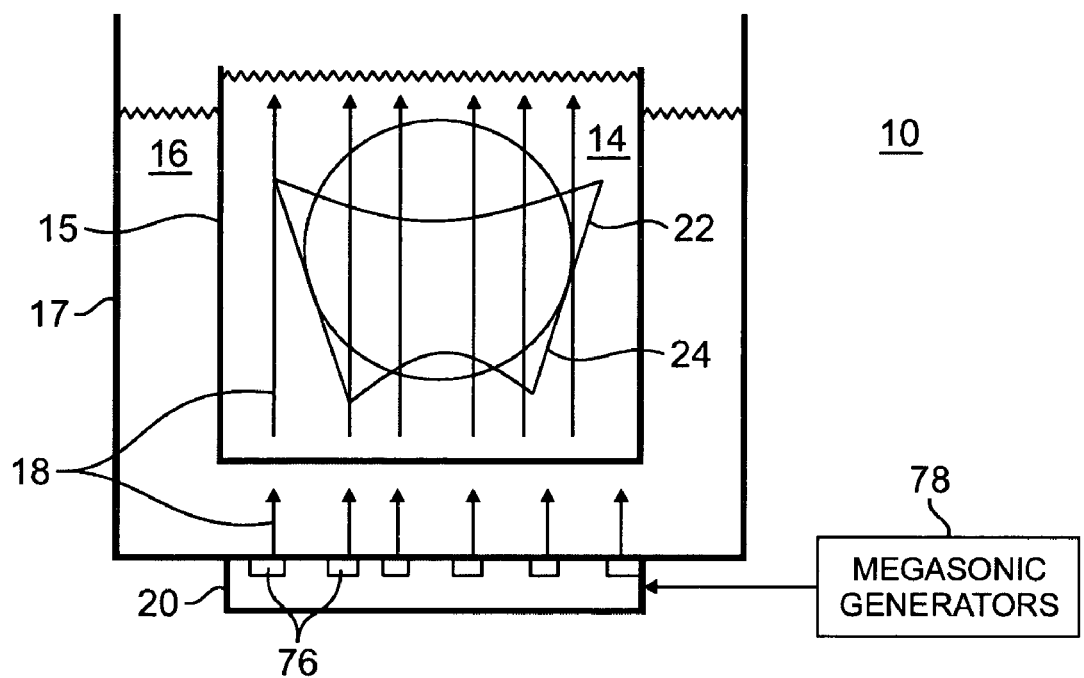
FIG. 1 illustrates a schematic view of an exemplary vibrational (e.g., megasonic or ultrasound) cleaning system that may benefit from techniques of the present invention.

FIG. 1 shows a schematic representation of an exemplary vibrational (e.g., megasonic or ultrasound) cleaning system 10 that may benefit from the techniques of present invention. In one exemplary embodiment, the vibrational cleaning system 10 comprises a process bath, such as may include an inner bath 14 in an inner tank 15 and an outer bath 16 in an outer tank 17. The vertical arrows 18 in FIG. 1 represent acoustic beams, such as may be generated by at least one acoustic transducer 20 disposed at the bottom (or at a side) of the outer tank 17. A wafer carrier 22 may be used for supporting a plurality of wafers 24 (e.g., up to fifty wafers or workpieces) to be processed during a single cleansing cycle. By way of example, the pattern of vibrational energy may exhibit a vertical gradient (the vibrational power level decreases as a function of distance) and may be affected by other factors. For example, the wafer carrier 22, typically constructed of a plastic, may absorb some of the vibrational energy. It will be understood that the vibrational cleaning system 10 illustrated in FIG. 1 should not be construed as limiting aspects of the present invention being that such a system represents just one example of various types of vibrational cleaning systems that may benefit from the techniques of the present invention.

The inventors of the present invention have innovatively recognized a technique for accurate and repeatable in-situ monitoring of the vibrational power level during a vibrational cleansing cycle. Aspects of the present invention avoid or reduce inaccuracies in the measurement of vibrational power level that can arise due to the interaction of the acoustic beams with the various structures that may be present in the process bath. Examples of such interactions may include the presence or absence of wafers, wafer interspacing, the physical characteristics of the mounting structure for the wafers, the characteristics of the liquid medium, etc.

Figure 2:
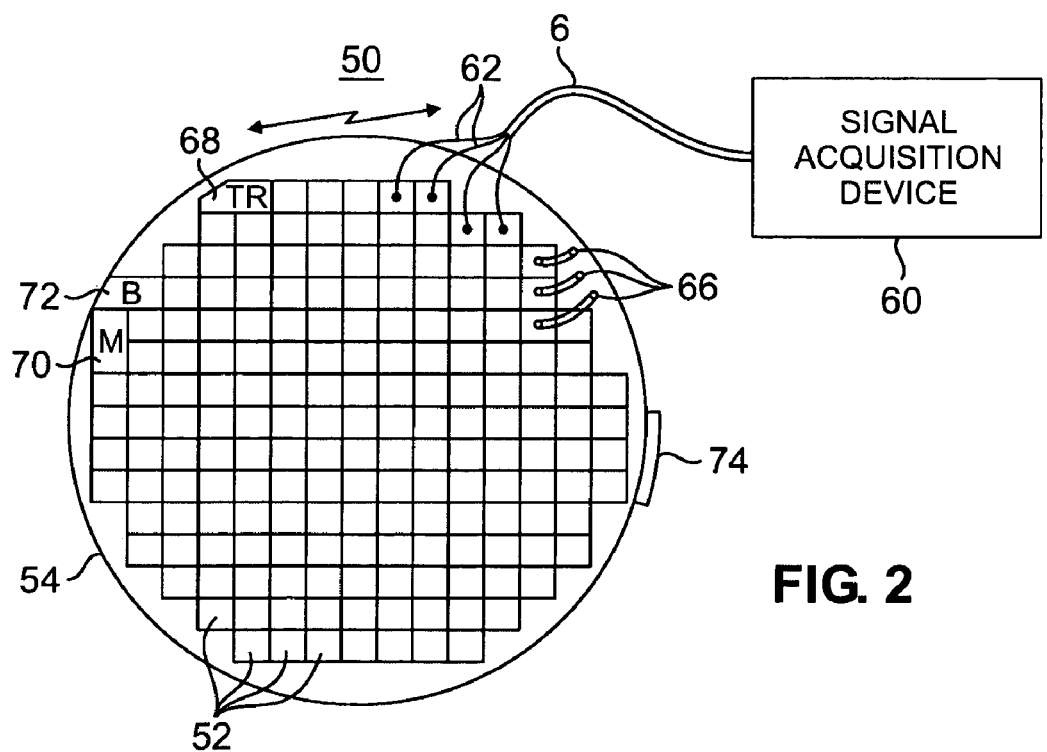
FIG. 2 in part illustrates a schematic view of an exemplary pressure-sensing device embodying aspects of the invention for in-situ measuring of vibrational energy in a process bath of the vibrational cleaning system of FIG. 1.

In one exemplary embodiment, as illustrated in FIG. 2, a pressure sensing device 50 embodying aspects of the invention comprises an array of pressure sensors 52 embedded in or otherwise disposed on a wafer 54, e.g., an array of pressure sensors embedded in a silicon substrate or individual sensors bonded to the wafer at selected locations. Essentially, the pressure-sensing device 50, from an acoustic load point of view behaves as any wafer workpiece in the process bath, and is conducive to a more accurate and repeatable monitoring of the levels of vibrational energy actually experienced by any of the workpieces undergoing vibrational processing.

The pressure-sensing device 50 can be formed in several ways. In one exemplary embodiment, cavities in a silicon wafer are etched out, and then monolithic pressure sensors are inserted and fixed using affixing techniques well understood by one skilled in the art.

In another exemplary embodiment, the pressure-sensing device may comprise a semiconductor wafer processed to integrally form an array of pressure sensors. That is, semiconductor wafer processing techniques (as may be generally used for the fabrication of VLSI (very large scale integration) circuitry) may be adapted to construct the array of pressure sensors by forming a wafer having a plurality of VLSI sensors as the components of the wafer. For readers desirous of general background information in connection with miniaturized pressure sensors as may be formed within a silicon wafer, see, for example, U.S. Pat. No. 6,629,465 titled "Miniature Gauge Pressure Sensor Using Silicon Fusion Bonding and Back Etching."

Accordingly, the expression "a test wafer comprising an array of pressure sensing elements disposed thereon" should be broadly construed to encompass either of various approaches, such as pressure sensors that may be inserted within the wafer, may be mounted on the surface of the test wafer, or may be integrally constructed within the wafer or any combination of the foregoing approaches. The basic concept is not necessarily the specific construction technique used for the pressure sensors but the ability to provide a plurality of pressure sensors in a wafer test device that is otherwise essentially undistinguishable from wafer work pieces normally processed in the process bath. It will be appreciated that the pressure-sensing device 50 may use MicroElectroMechanical Systems (MEMS) or any other type of sensor (e.g., piezoelectric) that is responsive to relatively rapid changes in pressure, as the upper range of megasonic frequency may be around 1 MHz or higher. That is, the time response of the sensor should be sufficiently fast for detecting dynamic pressure changes during each pressure wave. The output signals from the array of pressure sensors should be appropriately buffered to maintain good signal integrity at least up to a desired range relative to the edge of the pressure sensing wafer, e.g., in the order of up to 300 mm off the edge of the pressure sensing wafer.

Communications between the sensor array 52 and an external signal acquisition device 60 can be implemented through several possible communication means. First, in one direct form of communication, signal-carrying wires can be used. A hard-wired connection can be implemented in several ways. In one exemplary approach, individual wires 62 may be affixed (e.g., glued or otherwise affixed) onto the pressure-sensing wafer from each of several sensor elements to a location at the wafer exterior. At that location, all the wires from each sensor may be bundled together and anchored to form a cable.

It is contemplated that one need not connect every sensor element of the sensor array for any given application. For example, there may be applications where a user may desire to monitor the megasonic power over a desired region of the process bath and that user may want to utilize megasonic power readings just from sensor elements that correspond to that desired region. In this type of application, the user would just connect the wires from the desired sensor elements, as opposed to connecting the wires from each sensor of the sensor array. The sensor interface design is sufficiently user-friendly and versatile to accommodate the needs of such a user without undue time consuming and burdening interface operations. In another exemplary approach, electrically conductive pathways 66 may be printed onto the pressure-sensing wafer using standard printed circuit board (PCB) techniques.

It will be appreciated that the signal frequency from the pressure-sensing device is relatively low compared to signal processing speeds encountered in commercially available microelectronics devices. For example, compare 1 MHz for megasonic operation relative to a typical wireless system that may operate at 2 GHz. Accordingly, other approaches that are envisioned for communicating the pressure information may include wireless signaling from a transmitter (TX) 68 in the wafer, or by storing the pressure sensor readings in an internal memory device (M) 70 for subsequent download. In general one may utilize any sufficiently fast signal processing that allows for detecting dynamic pressure changes during each pressure wave. It will be appreciated that wireless approaches would require some suitable power supply, such as a battery 72, within or on the wafer 54 in order to power up the internal circuits, such as the transmitter 68 or memory device 70. In the wired approach, power would be supplied from an external power supply.

The outer surface of the pressure-sensing device 50 may be protected from chemicals in the process bath by a suitable coating 74, such as comprising oxide, nitride, polyimide, Teflon, etc.

Respective readings from every sensor in the sensor array can be processed to generate a map indicative of megasonic power readings across the pressure-sensing wafer during a given process configuration. By way of example and not of limitation, this map may allow for an optimal tuning between a vibrational energy generator and vibrational transducers responsive to the generator, as elaborated in greater detail below, for a given set of conditions in the process bath.

By way of example, a typical vibrational transducer 20 (FIG. 1) in a megasonic device may comprise an array of flat, segmented megasonic transducers 76 fed by one or more megasonic generators 78. To get maximum efficiency the transducers 76 should preferably be "matched" to the generator 78 for a given set of conditions, a process that is not easily accomplished when using prior art techniques, considering the various variables that can influence the actual megasonic power readings, such as vessel type, fluid level, number of wafers, inter-wafer spacing, etc. However, a map indicative of megasonic power readings across the pressure-sensing wafer, as can be obtained with a pressure-sensing device embodying aspects of the present invention, would provide information that allows a equipment designer to more accurately and consistently match individual transducers 76 to the megasonic generator 78. Additionally, for the case where there are multiple vibrational energy generators, such generators need to be substantially in phase with one another or one may risk canceling out the vibrational energy that is being applied. For example, adjacent to the wafer surface the vibrational energy comprises a succession of compressive waves forcing compression and expansion of any trapped gasses in the liquid medium. However, if neighboring generators were to become out of phase, wafer areas that receive overlapping acoustic beams from any such out-of-phase generators could experience virtually no compressive force. A map indicative of pressure readings across the pressure-sensing wafer would allow identification of any areas lacking compressive force.

While the preferred embodiments of the present invention have been shown and described herein, it will be obvious that such embodiments are provided by way of example only. Numerous variations, changes and substitutions will occur to those of skill in the art without departing from the invention herein. Accordingly, it is intended that the invention be limited only by the spirit and scope of the appended claims.

We claim as our invention:

1. Apparatus for in-situ measurement of vibrational energy applied to a wafer in a process bath of a vibrational cleaning system, wherein said apparatus comprises a test wafer comprising:
    an array of pressure sensing elements disposed thereon for monitoring power level variation of a time-varying pressure wave, said time-varying pressure wave indicative of vibrational energy that would be applied to a wafer in the process bath in the position of the test wafer; and
    a transmitter for wirelessly communicating the electrical signal from each pressure-sensing element.

2. The apparatus of claim 1 wherein said array of pressure sensing elements is disposed in a plurality of cavities etched in said test wafer.

3. The apparatus of claim 1 wherein said array of pressure sensing elements is integrally constructed in said test wafer.

4. The apparatus of claim 1 wherein said array of pressure sensing elements is bonded to a surface of the test wafer.

5. The apparatus of claim 1 wherein the vibrational energy is selected from the group consisting of ultrasonic and megasonic vibrational energy.

6. The apparatus of claim 1 wherein said test wafer is configured substantially identical to one or more wafer workpieces undergoing vibrational cleansing in said process bath.

7. The apparatus of claim 1 wherein said array of pressure sensing elements comprises microelectromechanical systems (MEMS) pressure sensing elements.

8. The apparatus of claim 1 wherein said test wafer comprises an outer coating for protecting the test wafer from chemicals that may be present in the process bath.

9. Apparatus for in-situ measurement of vibrational energy applied to a wafer in a process bath of a vibrational cleaning system, wherein said apparatus comprises a test wafer comprising:
    an array of pressure sensing elements disposed thereon for monitoring power level variation of a time-varying pressure wave, said time-varying pressure wave indicative of vibrational energy that would be applied to a wafer in the process bath in the position of the test wafer;
    a memory device for storing over a period of time the electrical signal from each pressure-sensing element.

10. A method for in-situ measuring of vibrational energy in a process bath of a vibration system used for cleansing one or more semiconductor workpieces, said method comprising:
    providing a test wafer with an array of pressure sensing elements; and monitoring with the array of pressure sensing elements power level variation of a time-varying pressure wave in said process bath; and
    wirelessly transmitting an electrical signal from each pressure-sensing element.

11. The method of claim 10 wherein the providing of a test wafer with an array of pressure sensing elements comprises disposing said array in a plurality of cavities etched in the test wafer.

12. The method of claim 10 wherein the providing of a test wafer with an array of pressure sensing elements comprises integrally constructing said array in the test wafer.

13. The method of claim 10 wherein the providing of a test wafer with an array of pressure sensing elements comprises bonding said array of pressure sensing elements to a surface of the test wafer.

14. The method of claim 10 wherein said test wafer is configured to be substantially identical to one or more workpieces undergoing vibrational cleansing in said process bath.

15. The method of claim 10 further comprising applying an outer coating for protecting the test wafer from chemicals that may be present in the process bath.

16. A method comprising:
    providing a test wafer with an array of pressure sensing elements;
    monitoring, with the test wafer, a pressure wave in a process bath used for cleaning a semiconductor workpiece, the pressure wave being formed by a plurality of transducers;
    processing an output signal from each of the pressure sensing elements to generate a map indicative of vibrational power readings corresponding to a plurality of locations on the test wafer; and
    matching individual ones of the plurality of transducers to a generator that powers the transducers.

17. The method of claim 16, wherein the generator is one of a plurality of generators that supply power to the transducers, and the method further comprises;
    using the generated map to identify if two of the plurality of generators are out of phase with each other; and
    causing the two generators to be substantially in phase with one another, in response to the identification.

18. A method for in-situ measuring of vibrational energy in a process bath of a vibrational system used for cleansing one or more semiconductor workpieces, said method comprising:
    providing a test wafer with an array of pressure sensing elements;

monitoring a pressure wave in said process bath using the test wafer;
processing an output signal from ones of the pressure sensing elements to generate a map indicative of vibrational power readings corresponding to a plurality of locations on the test wafer; and
using the generated map indicative of vibrational power readings for determining effects of different process tools in the process bath.

19. The method of claim 18 further comprising providing a memory device for storing over a period of time an electrical signal from each pressure-sensing element.

20. The method of claim 18, further comprising using the generated map indicative of vibrational power readings for evaluating process checks of the vibrational cleaning system that may be performed over a period of time.

* * * * *